United States Patent
McDaniel et al.

[11] Patent Number: 5,336,226
[45] Date of Patent: Aug. 9, 1994

[54] BONE FACE CUTTER

[75] Inventors: John M. McDaniel; Michael W. Kiser, both of Bloomington, Ind.

[73] Assignee: Chapman Lake Instruments, Inc., Bloomington, Ind.

[21] Appl. No.: 928,961

[22] Filed: Aug. 11, 1992

[51] Int. Cl.$^5$ .................. A61B 17/00; A61F 2/32
[52] U.S. Cl. .................................. 606/79; 606/86
[58] Field of Search .............. 606/79, 80, 86, 87, 606/88, 176, 177, 178, 179, 180, 183

[56] References Cited

U.S. PATENT DOCUMENTS

| | | | |
|---|---|---|---|
| 1,655,836 | 1/1928 | Hawkinson . | |
| 2,369,925 | 2/1945 | Smith | 606/82 |
| 2,785,673 | 3/1957 | Anderson . | |
| 3,630,204 | 12/1971 | Fishbein | 606/81 |
| 3,633,583 | 1/1972 | Fishbein | 606/81 |
| 3,702,611 | 11/1972 | Fishbein | 606/81 |
| 3,713,194 | 1/1973 | Danly . | |
| 4,004,581 | 1/1977 | Heimke | 606/82 |
| 4,273,117 | 6/1981 | Neuhauser | 606/81 |
| 4,467,801 | 8/1984 | Whiteside . | |
| 4,491,132 | 1/1985 | Aikins | 606/79 |
| 4,526,171 | 7/1985 | Schachur | 606/180 |
| 4,729,763 | 3/1988 | Henrie | 606/179 |
| 4,998,937 | 3/1991 | Grimes . | |
| 5,180,384 | 1/1993 | Mikhail | 606/79 |

*Primary Examiner*—Michael A. Brown
*Attorney, Agent, or Firm*—Woodard, Emhardt, Naughton Moriarty & McNett

[57] ABSTRACT

A power operable bone facing cutter has a body with a pilot hole or stem for orientation with the bone to be faced. A cutter disk is removably fastened to the working end of the body and has a cutting edge lying in a plane perpendicular to the pilot axis. The cutting edge extends from a circle centered on the axis, outward to an outer circular edge. The cutting edge is at an angle with respect to a radius from the axis to cut toward the axis as the cutter is rotated. A chip escape slot is provided in the disk and body above the cutting edge. The rest of the bottom surface of the cutter disk is flat to provide a supporting surface spaced at a gage height from the plane of the cutting edge to provide optimum cutting while the supporting surface prevents excessively rapid or deep cutting, thus producing a skiving action.

4 Claims, 5 Drawing Sheets

BONE FACE CUTTER

BACKGROUND OF THE INVENTION

1. Field of the Invention

This invention relates generally to orthopedic surgery, and more particularly to tools intended to provide smooth faces on bone surfaces to facilitate installation and anchoring of artificial joint implants and the like.

2. Description of the Prior Art

A U.S. Pat. No. 2,785,673 issued Mar. 19, 1957 to Anderson discloses a femoral prosthesis and method of installation of it. One of the steps in the procedure is to employ a facer tool 35 which has cutting blades 35' on its lower face as shown on FIG. 8. This tool is rotated on stem 34 to cut a flat face 37 at the upper end of the femur 22 on which the head 39 (FIG. 6) of the prosthesis can be seated.

A more recent U.S. Pat. No. 4,467,801 issued Aug. 28, 1984 to Whiteside shows a similar, hand operated plateau planer having an abraded surface 31 with a plurality of cutting ridges 32 (FIGS. 3 and 4) to provide a flat surface 62 on the tibia to receive and support a tibial prosthesis.

When such planing tools are used by hand, the procedure is comparatively slow and unsatisfactory. When such tools are powered, the tool performance is not particularly satisfactory. For example, there is an accumulation of bone cuttings which inhibit good cutting action. The tendency of the tool operator is to apply more pressure. This, combined with the additional time required, generates heat at the bone surface being treated, which can result in thermal damage to the bone. It can also cause bone perimeter damage, more particularly fragmentation at the edge of the surface. It is an object of the present invention to improve cutting efficiency for bone facing operations to reduce time and effort and avoid a tendency toward bone damage in such operations.

SUMMARY OF THE INVENTION

Described briefly, according to a typical embodiment of the present invention a power operated bone facing tool employs a stem which may either be an integral part of the tool itself or a separate part that is already installed in the bone and which is received in a pilot hole in the tool. This guides a cutter having an edge situated in a plane perpendicular to the axis the stem and extending outward from a circle at the stem to an outer circular edge. The edge does not extend on a radius from the axis but, instead, is disposed at an angle with respect to a radius to encourage movement of bone chips toward the axis as the tool is rotated and the chips move up a slot in the body of the tool and out. The rest of the bottom surface of the cutter is flat to provide a supporting surface spaced from the plane of the cutting edge a desired gage height so that the cutting edge provides optimum cutting while the supporting surface prevents excessively rapid or deep cutting. The cutter disk including the cutting edge and support surface is removable from the end of the cutter body as a unit for simple, quick and effective replacement without need to adjust cutting height on the replacement cutter upon or after installation on the cutter body.

DESCRIPTION OF THE PREFERRED EMBODIMENT

Figure 1:
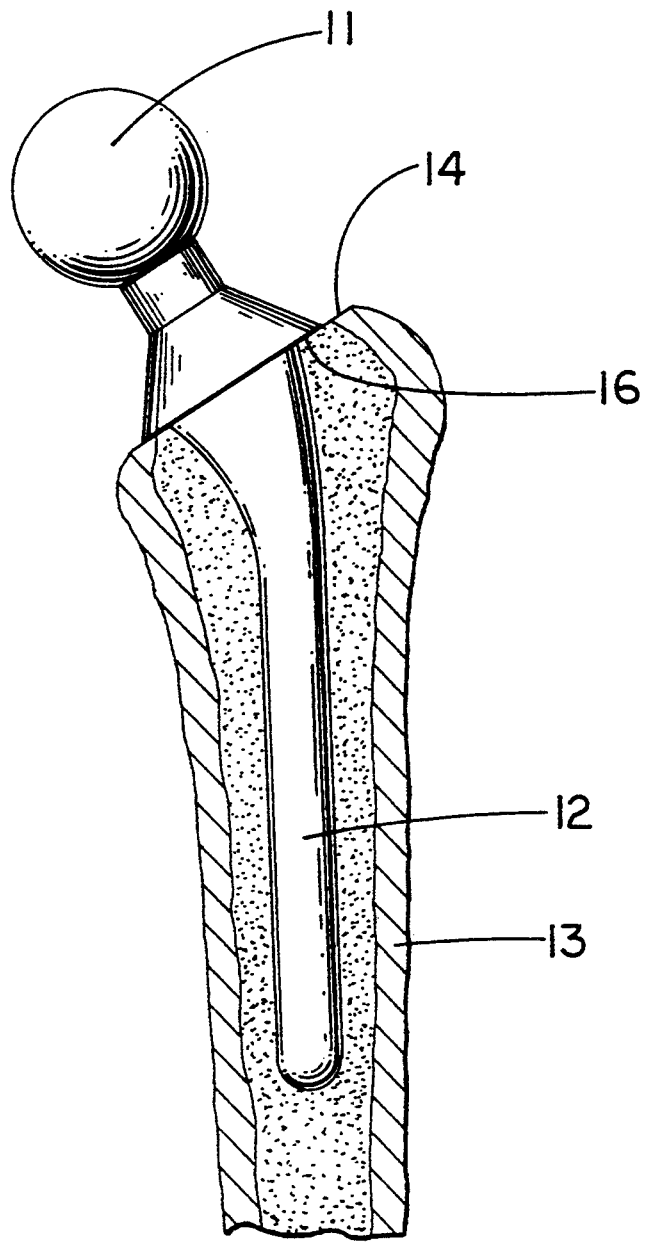
FIG. 1 is a schematic diagram of the upper portion of a femur with an artificial implant mounted in it.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 5:
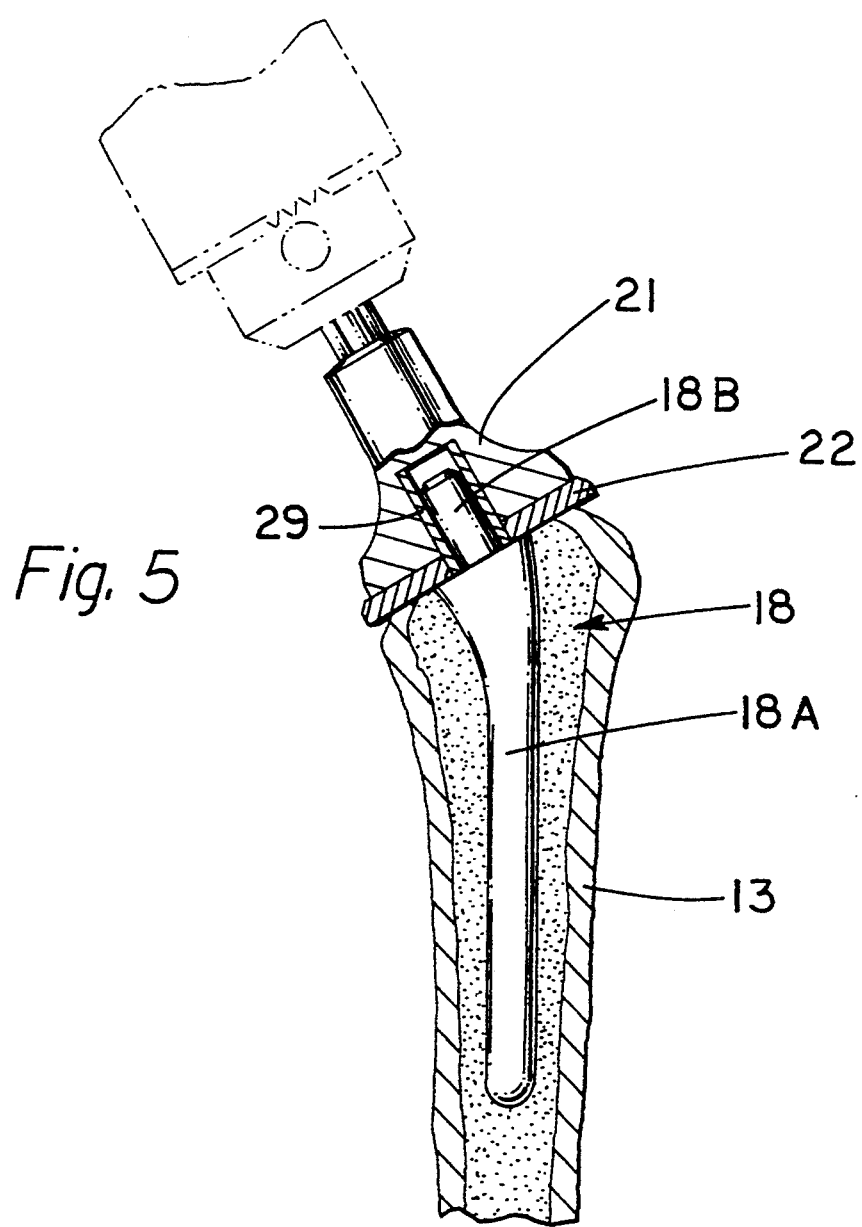
FIG. 5 is similar to FIG. 1 but showing this cutter operating on the femur while piloting on a stem atop a broach temporarily located in the site where the implant of FIG. 1 will later be situated.

Referring to the drawings, FIG. 1 is a schematic cross section through a femur with a hip joint prosthesis mounted in it. The prosthesis includes the ball 11 at the top for the hip replacement, and the shaft 12 received in the femur 13. Prior to implanting such a device, the natural deteriorated ball and bone structure atop the femur has been cut-off by a saw, leaving an unfinished surface slightly above where the desired finished face 14 will be. Then a hole is drilled in the femur and then enlarged and shaped with a series of specially shaped hand broaches of increasing size until the desired size and shape of hole for the implant is made in the femur. The broach 18 of the final and maximum size is shown in FIG. 5 with body 18A and stem 18B. When the broach has been employed to reach the final desired size of the hole in the femur, it is necessary that the seating face 14 on the top of the femur be smooth and flat for the shoulder 16 of the prosthesis to seat on it when the prosthesis is installed. About two millimeters of material removal may be adequate to achieve the desired smoothness and orientation.

The above description of prior art mentions two patents disclosing facing equipment and/or procedures. Another procedure is to use a powered hand drill chucking a rotary facing tool such as a spotface tool with a plurality of teeth on the end and radially extending from the center of it (such as in the above-mentioned patents), and a hole in the middle of the spotface tool received on a pilot stem such as 18B of a broach as in FIG. 5 herein. The broach stem 18B guides the facing tool as it is pushed against the irregular saw-cut surface at the top of the femur to dress it down to a smooth surface such as at 14 in FIG. 1.

As indicated above, the prior art facing procedure has not been very satisfactory. Rather than getting a good cutting action on the bone face, and although the facing tool has had a plurality of radially extending cutting edges on it, there has not been good cutting operation. The result is that the procedure has been slower and has generated heat to the point of causing some damage to the bone. Prior art tools and procedure have also caused perimeter fragmentation of bone. The present invention is intended to alleviate these problems.

Figure 2:
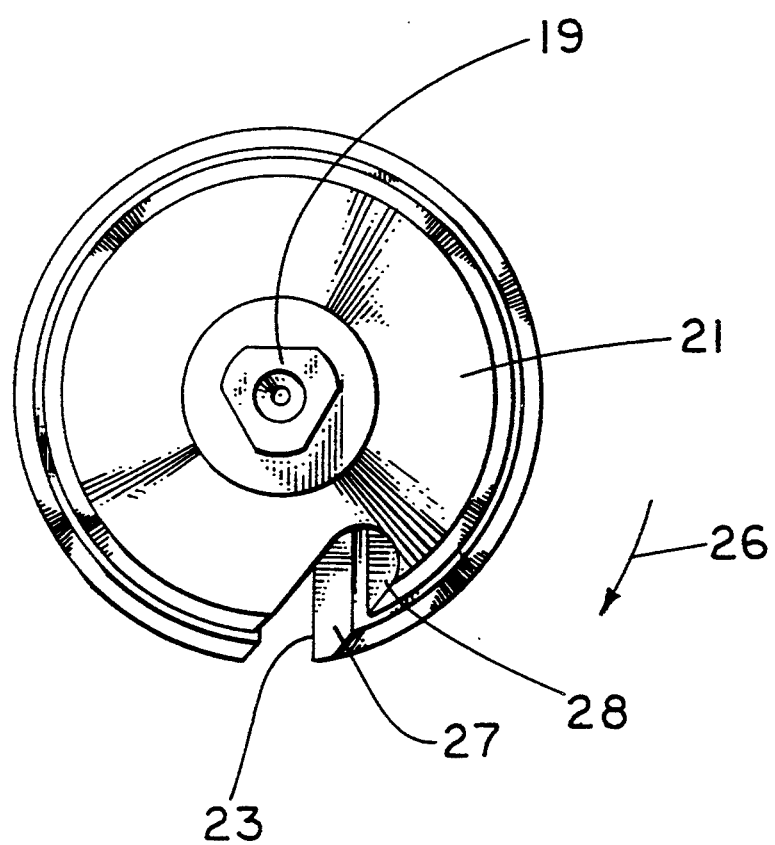
FIG. 2 is a top plan view of the bone face cutter according to a typical embodiment of the present invention.
Figure 3:
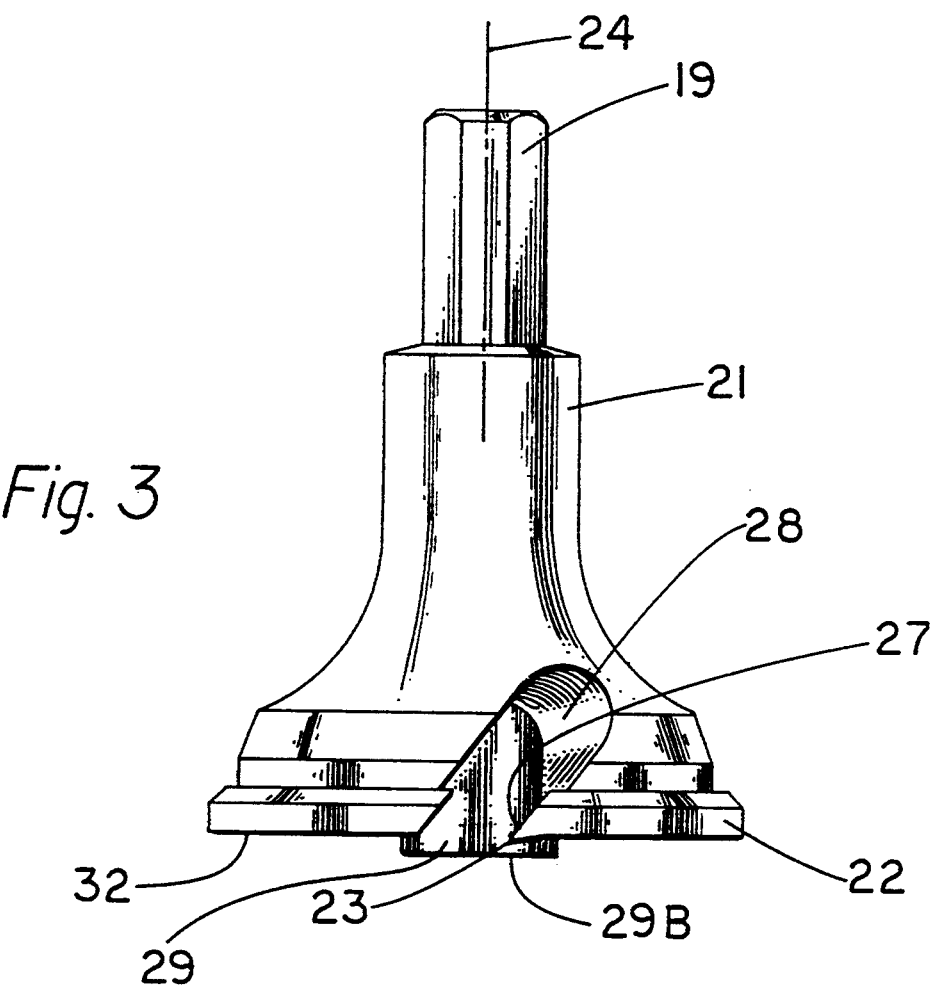
FIG. 3 is a front elevational view.
Figure 4:
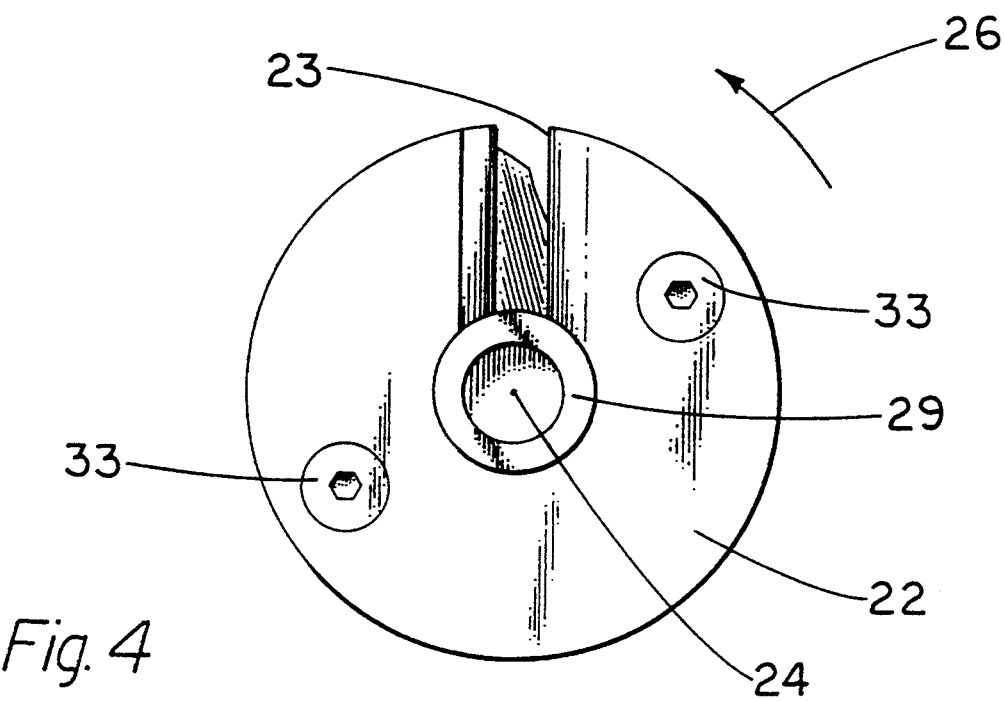
FIG. 4 is a bottom view thereof.

Referring now to FIGS. 2-4, these are top, front and bottom views of the calcar cutter of the present invention. The cutter includes a shaft 19 received in the electric drill chuck (FIG. 5). The cutter body 21 has the cutting disk 22 at the bottom of it. This disk is provided with a cutting edge 23 which, according to one feature of the invention, extends on a line that is not on a radius from the rotational center 24. Therefore, as the cutter rotates in the direction of arrow 26, portions of the cutting edge farther out toward the perimeter are at increasingly greater distances ahead of a radial line extending from the rotational axis through the innermost point on the edge. This geometry imparts a shearing, slicing action that is directed inward to minimize any tendency to fragment bone edges and also cuts more efficiently in general. Also, due to the somewhat bell shaped configuration of the body, the chips move up the ramp 27 and out the top through the slot 28 readily, the greater volume of chips produced near the perimeter having a shorter distance to travel up the ramp to escape the slot. The ramp angle is about 52 degrees up from the bottom face 32, thus providing a rake angle of 38 degrees from a plane normal to the plane of the face 32.

Figure 8:
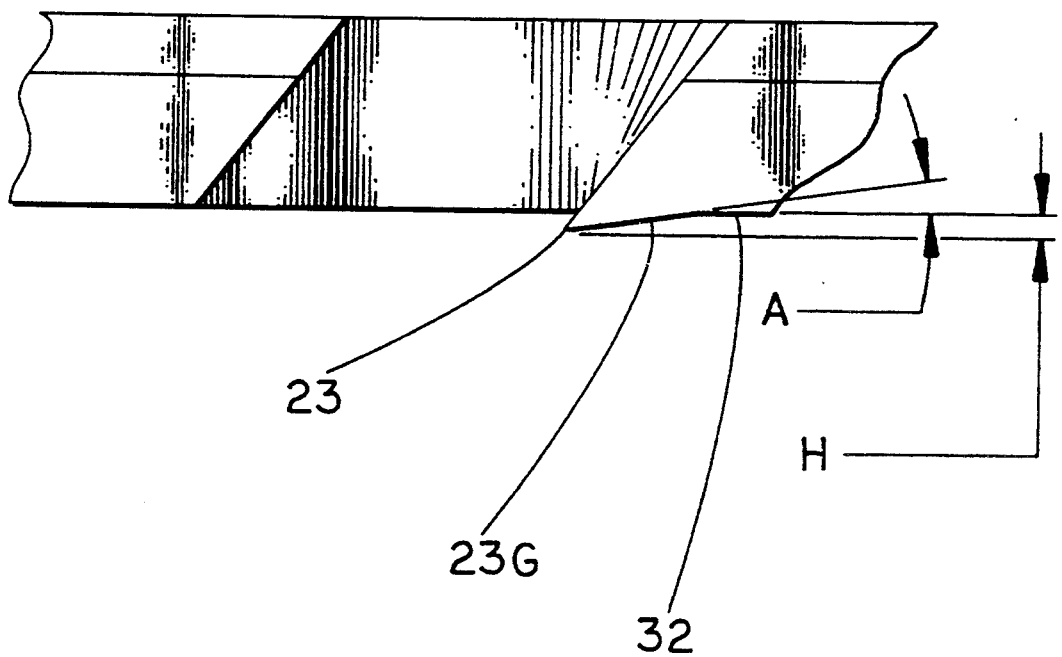
FIG. 8 is an enlarged fragmentary elevational view of the disk looking in line with the cutting edge.

A cylindrical socket insert bearing 29 is press fitted in cutter body 21, centered on axis 24. The bearing is received and guided on the guide post 18B of the broach in FIG. 5 as the cutting is done on the end of the bone. Because time cutting action is so efficient, only one cutting edge 23 is needed. The rest of the approximate 41 millimeter (mm) diameter face 32 of the disk except for the approximate 5 mm wide chip slot and the approximately 12.7 mm diameter center bushing hole, supports the tool on the bone structure so that the advance is not too rapid. The cutting edge 23 is spaced from the plane of face 32 by an amount referred to as "gage height" ("H" in FIG. 8). The lower end 29B of the bushing 29 should extend about 0.13 mm below cutting edge 23 so as to avoid the chance of the cutting edge contacting the top of the broach body 18A after the bone facing is sufficiently completed. This extension is shown exaggerated below the cutting edge 23 in FIG. 3. The clearance angle "A" (FIG. 8) is about eight degrees. When a new cutting edge is needed, the complete disk 22 is removed by removing the screws 33. The disks can be provided in assorted gage heights depending on preference of the surgeon and experience with the patient. A typical disk thickness is 3.30 mm. A gage height range considered satisfactory for the calcar trimmer is from 0.12 to 0.38 mm. The disk material is typically a 420 stainless steel which is hardened to 50-52 Rockwell "C" and on which the cutting edge 23 is ground at 23G.

When the bone facing is completed, the cutter is pulled off of the broach stem 18B. The broach is then pulled out of the femur, and the prosthesis is installed by conventional procedure.

Figure 6:
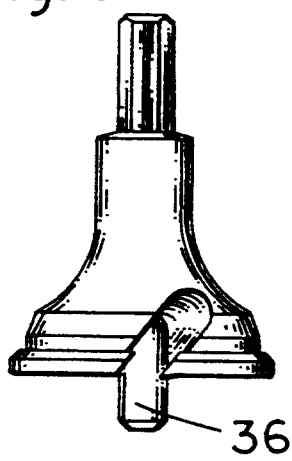
FIG. 6 is an elevational view similar to FIG. 3 but showing an alternative cutter for use on a patella.
Figure 7:
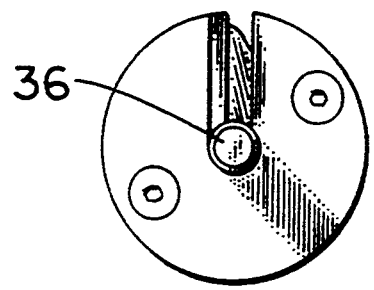
FIG. 7 is a bottom view thereof.

FIG. 6 shows another version of the tool. It is the patellar (kneecap) version. Instead of having the bearing 29 press fitted into it for reception on the pilot pin 18B during the cutting operation as in the version already described above, the FIG. 6 version has a pin 36 pressed into the axial hole in the body and extending from the bottom. This pin serves as a guide stem to be received in a guide hole previously drilled in a patella. The patella can be held while the FIG. 6 cutter is rotated by a powered hand drill and the cutter is guided by the cutter stem 36 in the predrilled guide hole in the patella. The gage height range considered preferable for the patellar trimmer is from 0.07 mm to 0.25 mm.

While the invention has been illustrated and described in detail in the drawings and foregoing description for two operations, one as a calcar trimmer for hip replacement operations, and the other as a patellar trimmer for knee replacement, the same is to be considered as illustrative and not restrictive in character, it being understood that only the preferred embodiment has been shown and described and that all changes and modifications that come within the spirit of the invention are desired to be protected.

what is claimed is:

1. A bone facing tool comprising:
   a body having one end for connection to a power drive, and having another end for working on bone;
   piloting means at the other end and defining a rotational axis perpendicular to the bone surface to be faced and having a piloting surface that is cylindrical about the axis;
   a cutter member secured to the piloting means and having a cutting edge lying in a plane perpendicular to the axis, the cutting edge beginning at an inner end point on a circle centered on the axis, and the cutting edge extending outward from the inner end point to an outer end point, the outer and inner end points being located on different radial lines from the axis; and
   a chip escape slot having an entrance defined by the cutting edge at one side of the entrance and by another edge of the cutter member at the other side of the entrance, the two edges being on opposite sides of a radius from the axis,
   the escape slot beginning at said perpendicular plane and extending generally axially from the plane on a slope from said another edge toward a second plane containing the axis and the radius.

2. The tool of claim 1 and wherein:
   the cutting edge is rectilinear, and the cutter member has a planar face parallel to the first-mentioned plane, the spacing between the first-mentioned plane and the plane of the face being between 0.07 mm and 0.38 mm.

3. The tool of claim 1 and wherein:
   the piloting means include a cylindrical stem projecting from the first-mentioned plane.

4. The tool of claim 1 and wherein:
   the piloting means include a cylindrical bushing intersecting the slot.

* * * * *